United States Patent
Chen et al.

(10) Patent No.: US 12,179,020 B1
(45) Date of Patent: Dec. 31, 2024

(54) SYSTEM AND METHOD FOR THE ACTIVATION OF ACTIVE ION TRANSPORTERS WITHOUT THE CONSUMPTION OF ADENOSINE TRIPHOSPHATE (ATP) MOLECULES FOR THE TREATMENT OF MUSCLE FATIGUE

(71) Applicant: University of South Florida, Tampa, FL (US)

(72) Inventors: Wei Chen, Tampa, FL (US); Jason Edward Mast, Plant City, FL (US); Pengfei Liang, Chapel Hill, NC (US)

(73) Assignee: University of South Florida, Tampa, FL (US)

( * ) Notice: Subject to any disclaimer, the term of this patent is extended or adjusted under 35 U.S.C. 154(b) by 407 days.

(21) Appl. No.: 17/697,350

(22) Filed: Mar. 17, 2022

Related U.S. Application Data

(60) Provisional application No. 63/162,172, filed on Mar. 17, 2021.

(51) Int. Cl.
*A61N 1/36* (2006.01)
*A61N 1/04* (2006.01)
*H01T 23/00* (2006.01)

(52) U.S. Cl.
CPC ....... *A61N 1/36034* (2017.08); *A61N 1/0456* (2013.01); *H01T 23/00* (2013.01)

(58) Field of Classification Search
CPC ... A61N 1/36034; A61N 1/0456; H01T 23/00
USPC ........................................................ 607/72
See application file for complete search history.

(56) References Cited

U.S. PATENT DOCUMENTS

| | | | |
|---|---|---|---|
| 4,165,750 A | 8/1979 | Aleev et al. | |
| 8,073,549 B2 * | 12/2011 | Chen | A61N 1/32 607/2 |
| 8,073,649 B2 | 12/2011 | Chen | |
| 2009/0054829 A1 * | 2/2009 | Chen | A61N 1/32 604/20 |

OTHER PUBLICATIONS

Taghian et al. "Modulation of cell function by electric field: a high resolution analysis" The Royal Society, Apr. 2015. pp. 1-11.
Blank, "Na,K-ATPase function in alternating electric fields" the FASEB Journal vol.$ Mar. 2020,. pp. 1-5.

(Continued)

*Primary Examiner* — Carl H Layno
*Assistant Examiner* — Michael J Lau
(74) *Attorney, Agent, or Firm* — Molly L. Sauter; Smith & Hopen, P.A.

(57) ABSTRACT

A system and method to control the Na/K pumps for the treatment or prevention of muscle fatigue by applying a synchronization modulation electric field that is effective in synchronizing the Na/K pumps down to individual steps throughout the pumping cycle, thereby synthesizing one ATP for each pumping cycle. The generated ATP molecule compensates the ATP consumed in extrusion of 3 Na ions and pumping 2 K ions such that the net-consumption of ATP for the Na/K pumps controlled by the system and method of the present invention is significantly reduced, theoretically to zero, thereby providing an effective treatment for muscle fatigue.

18 Claims, 11 Drawing Sheets

(56) References Cited

OTHER PUBLICATIONS

Di et al. "Effects of power frequency electric field exposure on kidney" Eco toxicology and Environmental safety 194 (2020) 110354, Feb. 2020. pp. 1-7.

Liu et al. "Activation of Na+ and K+ Pumping Modes of (Na, K)-ATPase by an Oscillating Electric Field" The Journal of Biological Chemistry vol. 265, No. May 13, 1990. pp. 1-9.

Chen et al. "Electrical Activation of Na/K Pumps Can Increase Iconic Concentration Gradient and Membrane Resting Potential" J. Membrane Biol. 214, 147-155 Dec. 2007 pp. 1-9.

Dreibati et al. "Influence of electrical stimulation frequency on skeletal muscle force and fatigue" Annals of Physical and Rehabilitation Medicine 53 (2010) 266-277. January pp. 1-12.

Liang, "The modified Synchronization Modulation technique revealed mechanisms of Na,K-ATPase" ProQuest LLC (2019) Mar. 2019, pp. 1-103.

McKenna et al. "Muscle K+, Na+, and Cl-disturbances and Na+ -k+ pump inactivation implications for fatigue" J, App Physiol 104: 288-295, 2008. Oct. 2007, pp. 1-8.

Jeon et al. "Effects of pulse duration on muscle fatigue during electrical stimulation inducing moderate-level contraction" Muscle Nerve 57: 642-649,2018. Aug. 2017 pp. 1-8.

Tran et al. "Synchronization Modulation Increases Transepithelial Potentials in MDCK Monolayers through Na/K Pumps" Plos one Apr. 2013, pp. 1-9.

\* cited by examiner

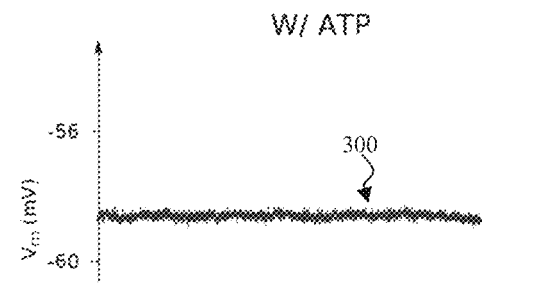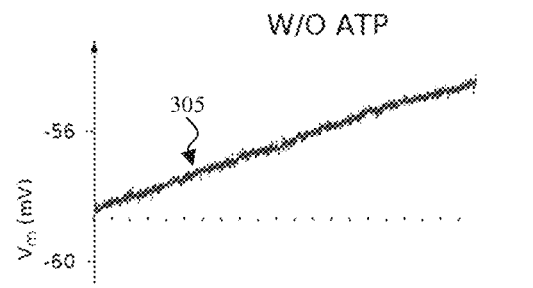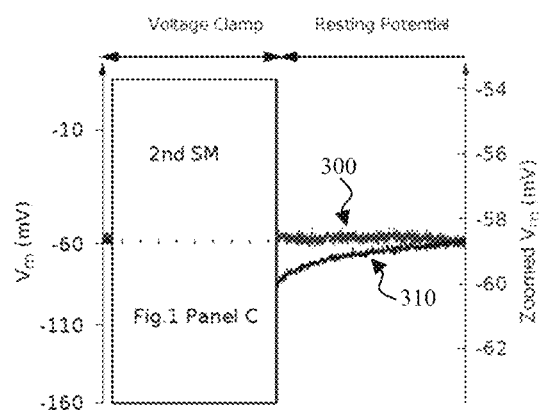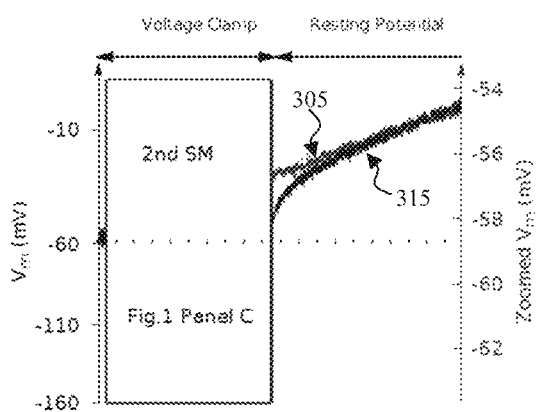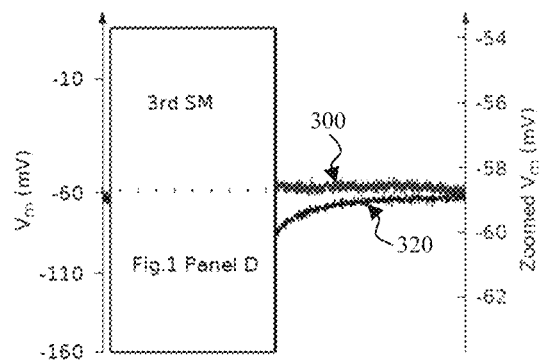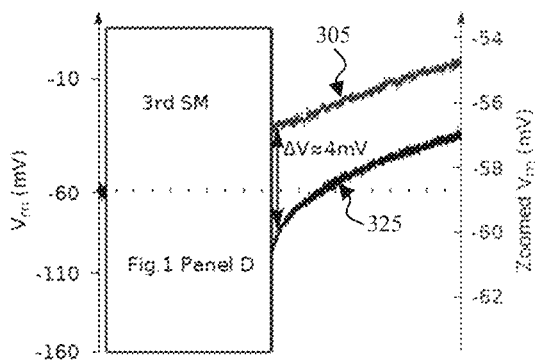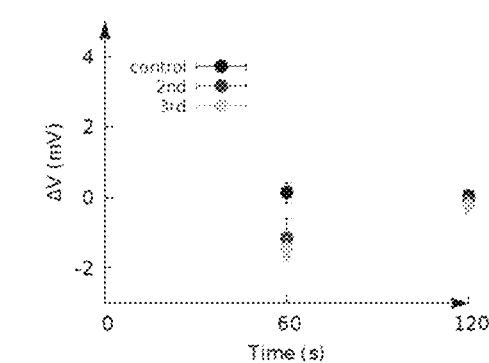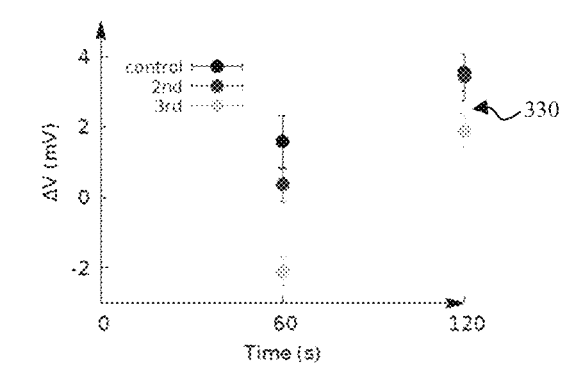
FIG. 3A                FIG. 3B

SYSTEM AND METHOD FOR THE ACTIVATION OF ACTIVE ION TRANSPORTERS WITHOUT THE CONSUMPTION OF ADENOSINE TRIPHOSPHATE (ATP) MOLECULES FOR THE TREATMENT OF MUSCLE FATIGUE

CROSS-REFERENCE TO RELATED APPLICATIONS

This application claims priority to U.S. Provisional Patent Application No. 63/162,172 filed on Mar. 17, 2021, and entitled, "SYSTEM AND METHOD UTILIZING ELECTRICAL ENERGY TO FUEL AND ACTIVATE ACTIVE ION TRANSPORTERS WITHOUT CONSUMPTION OF ADENOSINE TRIPHOSPHATE (ATP) MOLECULES: CLINICAL MUSCLE FATIGUE APPLICATION", which is incorporated by reference herein in its entirety.

BACKGROUND OF THE INVENTION

In living systems there are many active ion-transporters, such as electrogenic pump molecules and active ion-exchangers in cell membranes. These active ion-transporters maintain the specific ionic concentrations in the cell as well as the ionic concentration gradients across the cell membrane, wherein ionic concentration gradients result in an electrical potential across the cell membrane. The ionic concentration gradients and the membrane potential constitute electrochemical potential across the cell membrane, which is critical to many cell functions.

The electrochemical potential is the source for the generation and propagation of the action potential for all of the excitable cells, such as nerve cells, skeletal muscle fibers, and cardiac cells. This electrochemical potential also provides energy to many other active transporters, such as the Na/H exchangers that influence pH value. The ionic concentration gradients also play a significant role in controlling the cell volume and homeostasis. Therefore, maintaining the ionic concentration gradients and the membrane potential is critical to living cells.

The Na/K pump, or Na/K ATPase, is one of the most prevalent house-keeping proteins that is found within the membrane of almost every cell. The Na/K pump extrudes three Na ions out of the cell via the exchange of two K ions and consumption of one adenosine 5'-triphosphate (ATP) during each pumping cycle in order to maintain the ionic concentration gradients and the cell membrane potential. The Na/K pump is a unique energy converter which converts ATP hydrolysis energy to the electrochemical potential difference across the cell membrane so that the membrane proteins can easily use the energy.

Many diseases, or non-physiological conditions, are directly related to dysfunction of the Na/K pump. Exemplary diseases include various cardiac diseases, kidney diseases, especially the ischemia-induced kidney failures and kidney-related hypertension, diabetes induced ulcer, Alzheimer diseases and muscle fatigue.

Since Na/K pumps involve ion transportation across the cell membrane, the pumps are sensitive to the membrane potential. In the last a few decades, significant efforts have been made to electrically control or manipulate the ion pump functions. However, a practical technique is not currently available that can effectively activate the Na/K pump functions at physiological running condition. Once the ATP molecules are insufficient, the pump function will be significantly reduced.

Accordingly, what is needed in the art is a system and method for improves the pumping function of active ion transporters.

SUMMARY OF THE INVENTION

In various embodiments, the present invention provides a system and method for controlling the Na/K pumps by applying a 3rd generation synchronization modulation electric field ($3^{rd}$-SMEF), wherein the Na/K pump not only actively extrude 3 Na and pumping in 2 K ions by consuming one ATP molecule, but also synthesizes one ATP in each pumping cycle so that the ATP consumption is significantly reduced, theoretically to zero.

In one embodiment, the present invention provides a method for controlling one or more active ion transporters for the treatment or prevention of muscle fatigue. The method includes applying an oscillating electric field to an active ion transporter of one or more muscle tissues, wherein applying oscillating electric field includes applying a synchronization phase to synchronize the active ion transporters to a physiological turnover rate of the active ion transporters down to individual steps within a running cycle with a net-consumption of adenosine triphosphate (ATP) substantially equal to zero, applying a modulation phase to modulate the synchronized active ion transporters to a predetermined target turnover rate and applying a maintenance phase to maintain the synchronized active ion transporters at the predetermined target turnover rate for a predetermined duration of time.

In the method of the present invention, one ATP molecule is consumed during the running cycle of the one or more active ion transporters and one ATP molecule is synthesized during the running cycle of the active ion transporters, resulting in the net-consumption of ATP of the active ion transporters being substantially equal to zero during the running cycle.

In a particular embodiment, the active ion transporters are Na/K pumps.

In an additional embodiment, the present invention provides a system for controlling an active ion transporter for the treatment or prevention of muscle fatigue. The system includes an electric field generator to generate and apply an oscillating electric field to one or more muscle tissues, wherein the oscillating electric field comprises three serially applied phases. The application of the three serially applied phases of the oscillating electric field include, applying a synchronization phase to synchronize the active ion transporter to a physiological turnover rate of the active ion transporter down to individual steps within a running cycle with a net-consumption of adenosine triphosphate (ATP) substantially equal to zero, applying a modulation phase to modulate the synchronized active ion transporter to a predetermined target turnover rate and applying a maintenance phase to maintain the synchronized active ion transporters at the predetermined target turnover rate for a predetermined duration of time.

In another embodiment, the present invention provides a computer-readable medium storing a set of instructions configured for being executed by at least one processor for performing a method for controlling one or more active ion transporters. The method includes, controlling an electric field generator to apply an oscillating electric field to one or more muscle tissues, wherein the oscillating electric field comprises three serially applied phases. The three serially applied phases include, applying a synchronization phase to synchronize the active ion transporter to a physiological turnover rate of the active ion transporter down to individual steps within a running cycle with a net-consumption of adenosine triphosphate (ATP) substantially equal to zero, applying a modulation phase to modulate the synchronized active ion transporter to a predetermined target turnover rate and applying a maintenance phase to maintain the synchronized active ion transporters at the predetermined target turnover rate for a predetermined duration of time.

In specific embodiments, the oscillating electric field of the present invention can be used to treat or prevent muscle fatigue.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3A illustrates the waveform of the synchronization phase, or first phase, of the 3rd generation synchronization modulation electric field, in accordance with embodiments of the present invention.

FIG. 3B illustrates the waveform of the modulation phase, or second phase, of the 3rd synchronization modulation electric field, in accordance with embodiments of the present invention.

DETAILED DESCRIPTION OF THE INVENTION

Figure 1:
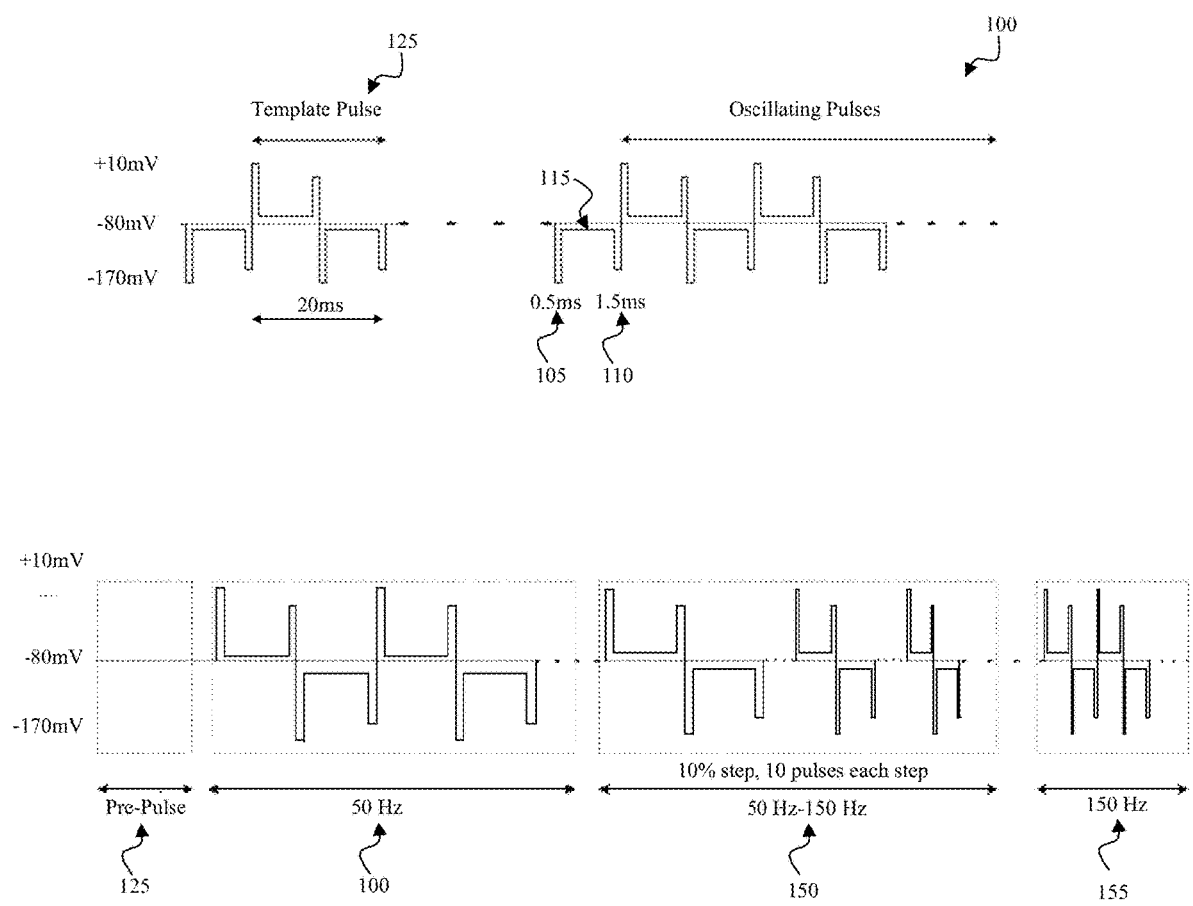
FIG. 1 illustrates the waveform of the present invention, the 3rd generation synchronization modulation electric field, in accordance with embodiments of the present invention.

In various embodiments, the present invention provides a system and method for controlling an active ion transporter for the treatment of muscle fatigue by applying an improved synchronization modulation electric field which not only drive the transporters to actively transport ions by consuming ATP, but also providing electric energy to the active transporters so that the transporter can synthesize one ATP in each running cycle. As a result, the electric energy substitutes the ATP hydrolysis energy to fuel the active ion transporter to actively transport ions across the cell membrane, without requiring ATP consumption.

Sodium-potassium (Na/K) pumps are known in biology to be one of many active ion transporters. In the following detailed description, the Na/K pump is used as an example of the process for controlling an active ion transporter. However, the description does not require any specific characteristics of the pump molecules, thus it is within the scope of the present invention to control other active ion transporters by the specially designed energy generating synchronization modulation electric field, as described.

Na/K ATPases, or Na/K pump, is a prevalent active transporter in almost all kinds of cells. In operation, the pump extrudes 3 Na ions by exchanging 2 K ions to build up Na and K concentration gradients and the potential difference across the cell membrane, thereby providing the critical environment for living cells. The energy stored in the ionic concentration gradient is the source for many member proteins. For example, ion channels utilize the membrane potential to generate and propagate the action potential. Various secondary active transporters use the energy to actively transport sugars, amino acid, etc. From the viewpoint of a physicist, the Na/K pump is a unique energy converter converting ATP hydrolysis energy to the electrochemical potential difference across the cell membrane, so that the membrane proteins can easily use the energy.

Because Na/K pumps involve ion-transports across the cell membrane, they are sensitive to the membrane potential. In the last few decades, significant efforts have been made to electrically control or manipulate the pump functions. Previously, red blood cells have been studied and was found that a weak oscillating electric field, at a frequency of about 1.0 MHz and 1.0 KHz, can activate the Na- and K-transports, respectively. It was also found that an AC current can either stimulate or inhibit the ATP hydrolysis activity of enzymes, depending on the Na/K ratio. However, there are currently no practice techniques available that can effectively activate the Na/K pump functions while also conserving ATP molecules.

The energy generating synchronization modulation electric field, or the 3rd generation synchronization modulation electric field, of the present invention is a practical technique that can effectively activate the function of Na/K pumps to develop the ionic concentration gradient and the membrane potential with less, or even zero, ATP-consumption. Moreover, the synchronization techniques were developed based on the dynamic model of the pump molecules. The successful synchronization modulation of the pumping rate and the substitution of ATP energy to fuel the pumping in the buildup of the ionic concentration gradients and the membrane potential support the dynamic model of the Na/K pumps as a microscopic machine.

In a particular embodiment, a method of controlling an active ion transporter can be applied to reduce muscle fatigue in a subject of interest. Fatigue is an important public health problem for a large portion of the population, especially for people having the occupation of athlete, soldier, and heavy-duty worker. Fatigue has been associated with decreased physical functioning and declined ability to manage routine daily activities. Studies have showed that up to 38% of community dwelling individuals and 43% of primary care patients experience significant fatigue. In the United States, workers with fatigue cost employers $136.4 billion annually in lost productivity. The situations become severe for the patients with various diseases, including, but not limited to, cancer, heart failure, diabetes, chronic fatigue syndrome, inflammatory diseases such as rheumatoid arthritis and multiple sclerosis. Fatigue not only affects muscle contraction but also the functioning of the brain and immune systems.

When compared with that in healthy animals, a decrease in Na and K concentration gradients across the cell membrane in exercising muscle is augmented in myocardial infarction in rats, likely due to an attenuation of Na/K pump activity. In muscle fibers, there are large number of Na/K pumps. Multiple studies have shown a close relationship between muscle excitability (as represented by M wave area), contractility (represented by tetanic force), and activity of the Na/K pumps (as activated by salbutamol and insulin).

There are three factors that affect the pump functions: i) lack of the ATP hydrolysis energy to fuel the pump cycles such as exhaust exercises, ischemia, and heart failure; ii) malfunction in the regulation system, especially in diabetes; and iii) deficit in the number of pump molecules, for instance the lumen membrane wall fallen in kidney nephron.

Among these factors, the most popular common is the lack of ATP molecules. A large amount of ATP hydrolysis energy is required for muscle contraction, including fueling the Na/K pumps to generate action potential and activate movements of action and myosin. It has been estimated that, at rest, Na/K pumps consume 40% of the ATP energy in the body. This percentile significantly increases when the muscles contract. It is known that pump molecules can be chemically activated making muscles more tolerant to the elevated K concentration. However, this can only happen in the presence of enough ATP molecules. Once the ATP molecules are insufficient, no one can activate the pump molecules.

Any factor that reduces the ATP concentration will decrease the muscle excitability and contraction endurance. Multiple studies have shown that the maximal Na/K pump activity is reduced after exhausting exercises, including sustained submaximal isometric contractions of single muscles, an athlete dynamic sprints or quadriceps contractions, a soldiers' heavy duty in combat field. Repetitively firing action potential and muscle contractions consume large amount of ATP Molecules resulting in the ATP depletion and lactic acid accumulation. The functions slowing down quickly increase the extracellular K and intracellular Na concentrations, which markedly affects the excitability of cell membrane and therefore the muscle contractility.

Clearly, ATP concentration and functions of Na/K pumps play a significant role in muscle fatigue. Activation of the pump molecules especially in the situation of insufficient ATP supply, then becomes the first priority in treatment of muscle fatigue.

The following experimental results illustrate that the 3rd generation synchronization modulation electric field technique of the present invention can hyperpolarize the membrane potential of skeletal muscle fibers, maintain the membrane potential in the situation of a hyperkalmia situation, prevent or alleviate the muscle fatigue for both the single muscle fibers and whole muscles, as well as for human beings performing exhaustive exercises or operating in physically overloaded working conditions.

In the following groups of experiments, the 3rd generation synchronization modulation electric field of the present invention was applied to frog skeletal muscle fiber from twitch semitandonosis muscles. The experiments were conducted using the double-Vaseline gap voltage-clamp technique. Single fibers were hand dissected from the muscles and mounted on a customer-made chamber. The membrane potential across the cell membrane was held at −90 mV and the synchronization modulation electric field was applied to the fibers by the voltage-clamp. Before and right after the field-application, the membrane potential was measured.

The present invention, the $3^{rd}$ SMEF consists of three phases, Phase 1 is to synchronize the Na/K pumps down to the individual steps throughout the pumping cycle in actively transporting Na and K ions without ATP consumption. Phase 2 is to modulate the pumping rate of the synchronized pump molecules to a pre-determined target value. Phase 3 is to maintain the pumping rate at the target value for certain period based on the clinical requirement.

FIG. 1 illustrates the waveform of the present invention, referred to herein as the $3^{rd}$ generation synchronization modulation electric field. In the synchronization phase 100, the electric field is a pulsed, symmetric, oscillating electric field consisting of two overshoot electric pulses in each half-cycle. First, is the activation overshoot electric pulse 105 with a duration of about 0.5 ms, or less, and a magnitude greater than about 90 mV followed by a plateau 115 of about 20 mV. Next, is the energy-trap overshoot electric pulse 110 having a duration of about 1.5 ms, or less, and a magnitude of about 70 mV.

It is noted that the magnitude of the electric field illustrated in FIG. 1 is applicable to the voltage-clamp experiments, or the potential difference across the cell membrane. For clinical applications, the applied field-strength should be adjusted to apply the proper electric field for the situation of the tissues and organs. The oscillating frequency is comparable to the natural turnover rate of the transporter used to synchronize the active ion transporters, or the Na/K pumps.

Also shown in FIG. 1 is a pre-pulse 125 that may be applied before the application of the oscillating electric field. The pre-pulse has the same waveform as the oscillating pulses. The pre-pulse 125 is used when the synchronized pump currents need to be identified. The currents generated by the pre-pulse 125 serve as the template to be subtracted from the currents generated by the individual oscillating pulses, with the resulting difference being the synchronized pump currents.

As such, the three phases of the oscillating electric field, in accordance with embodiments of the present invention, are illustrated in FIG. 1, wherein the pre-pulse 125 and the synchronization phase 100 are shown, as previously described, in addition to the modulation phase 150, where the oscillating frequency is gradually increased from about 50 Hz to about 150 Hz in a stepwise pattern, and the maintenance phase 155, where the field oscillating frequency remains at the target frequency.

In the modulation phase 150, the synchronization frequency or the frequency of the oscillating electric field will be gradually changed, going up or going down, to progressively modulate or entrain (accelerate or decelerate) the pump molecules to a pre-determined pumping rate. The waveform remains the same as that in the synchronization phase, and the oscillating frequency is gradually increased or decreased in a stepwise pattern (3% to 10% of the frequency change for 10 to 20 oscillating pulses) to a target frequency. By carefully maintaining the pump synchronization and gradually increasing or decreasing the synchronization frequency, the pump molecules can be entrained to higher and higher, or lower and lower, pumping rate, respectively, to reach a pre-determined value.

For the maintenance phase of the $3^{rd}$ SMEF, the frequency of the oscillating electric field will be kept at the target frequency for a certain time, based upon the requirement. The waveform of the oscillating electric field remains unchanged.

For future applications, the 3rd-SMEF has been specifically designed to avoid side effects on the cell membrane. For example, to avoid changing integrity of the cell membrane, the field-induced membrane potentials are in physiological range, much lower than the thresholds of membrane electroporation and protein denature. The short duration of the overshoot pulses (a few hundred microseconds) is not long enough to open the voltage-gated ion channels, including the Na-channels having the fastest electric response, or affect other membrane proteins. The oscillating waveform of the 3rd-SMEF was specifically designed for Na/K pumps, transporting cations to the opposite directions, and 50 Hz frequency is comparable to the turnover rate of Na/K pumps which is far away from other pumps, such as Ca2+ pump of 500 Hz.

The following experimental results show that the $3^{rd}$ generation forward synchronization modulation electric field can hyperpolarize and maintain the membrane potential of smooth muscle cells and skeletal muscle fibers in order to prevent or alleviate muscle fatigue for both individual muscles and for human beings performing exhaustive exercises or overload working.

In a study of the effects of the synchronization modulation electric field on the membrane potential of smooth muscle cells, the forward synchronization modulation electric field (target frequency of 500 Hz) was non-invasively applied on rat mesenteric arterioles blood vessels and the membrane potential change in the smooth muscle cell of the blood vessel was measured by a microelectrode. Before the electric field application, the natural membrane potential is about −38 mV, as shown in illustration 200 of FIG. 2. Beginning at about 1.8 seconds, the electric field was applied to the vessel, wherein the electric field consists of 100 synchronization pulses of 50 Hz followed by the modulation pulses where the frequency gradually increases, 3% for every 10 pulses up to 500 Hz. The magnitude of the electric field remained the same throughout the electric field-application.

Within the synchronization stage and early modulation stage (up to the 5th or 6th second), the membrane potential oscillates with respect to the physiological membrane potential of −30 mV. In other words, the average of the oscillating membrane potential remains at the natural membrane potential. Next, the profile of the oscillating membrane potential gradually shifted in the negative direction, indicating that the average of the membrane potential became more negative, especially at the end of the modulation stage. At the point a little over nine seconds where the frequency reached the maximum of 500 Hz, the membrane potential shifted to the maximum value of −45 mV, which remained the same until removal of the electric field.

Figure 2:
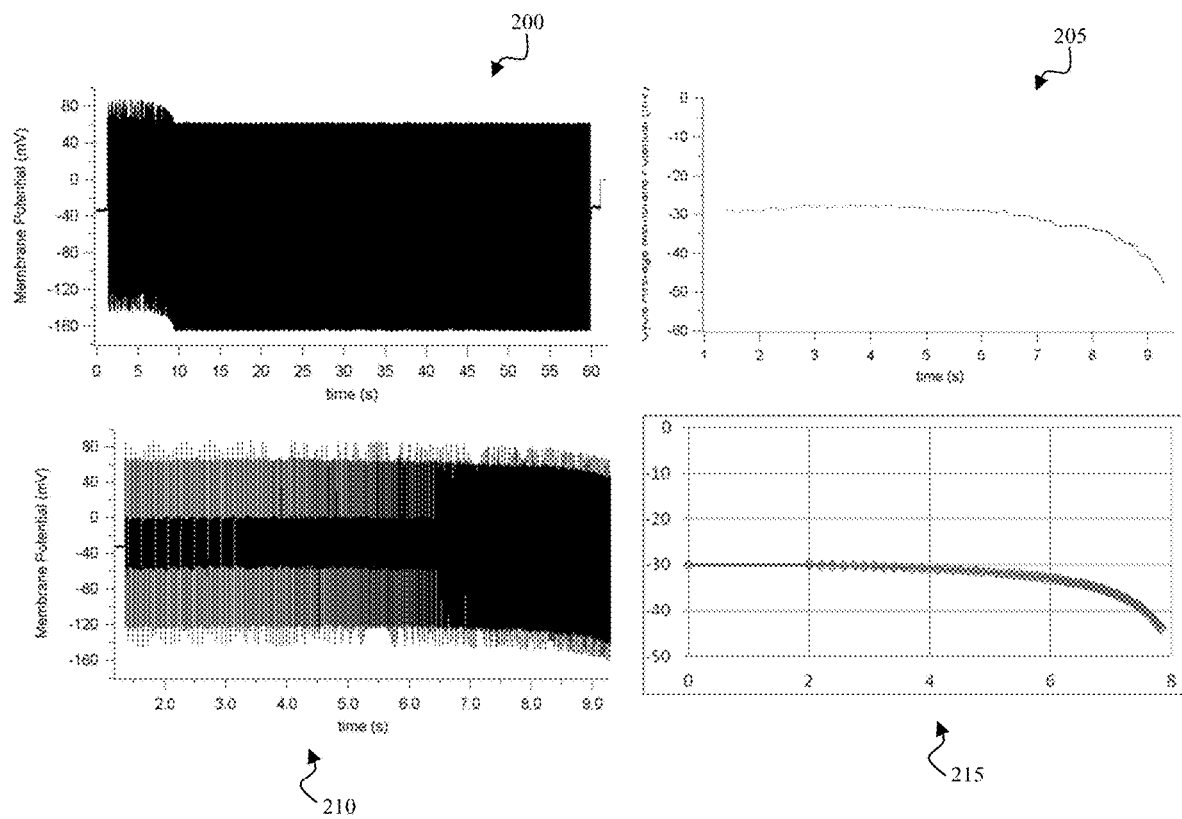
FIG. 2 illustrates the membrane potential changes of smooth muscle cells in response to the synchronization modulation electric field, in accordance with embodiments of the present invention

The potential change during the modulation stages is shown in illustration 210 of FIG. 2. The average of the oscillating membrane potential vs. time is shown in illustration 205 of FIG. 2. The membrane potential change estimated by the pumping rate based on the synchronization modulation frequency is shown in illustration 215 of FIG. 2. The trends of the time-course of the pumping rate calculated based on the changes in the field frequency fits very well to the average value of the field-induced oscillating membrane potential shown in illustration 205 of FIG. 2. The similar trends in 205 and 215 indicate that the membrane potential change is due to the pumping rate acceleration.

This result confirms that the membrane potential hyperpolarization is due to acceleration of the pumping rate induced by the synchronization modulation electric field of the present invention.

In another experiment, the effects of the method of the present invention on the maintenance of the membrane potential of skeletal muscle fibers were analyzed. The function of Na/K pumps is to maintain ionic concentration gradients across cell membrane, which can be expressed as the Na and K equilibrium potentials. The membrane potential is a weighted summation of the positive Na-equilibrium potential and negative K-equilibrium potential. Because the membrane leakage for K ions is much larger than that for Na ions, the membrane resting potential is mainly determined by the K-equilibrium potential. Due to the leakage of cell membranes, the ionic concentration gradients are inevitably gradually reduced, or the membrane potential is depolarized. At physiological conditions, functions of the Na/K pumps compensate the membrane leakage to maintain the membrane resting potential. However, once the pumps somehow stop running, the membrane potential will be slowly, but continuously, depolarized. On the other hand, activation of the Na/K pumps which increases the K concentration gradient, or the value of K-equilibrium potential should hyperpolarize the membrane potential.

FIG. 3A and FIG. 3B illustrate the membrane potential changes in the normal physiological or in the presence of extremely low ATP molecules, respectively, with or without the application of the $3^{rd}$ SMEF, the present invention. Traces 300 and 305 represent the control without the electric field application of the present invention. As shown, in the presence of physiological ATP concentration (300), Na/K pumps run well so that the membrane potential remains at a constant value of about −58.5 mV. However, in the presence of extremely low ATP molecules (305), the membrane potential gradually depolarized to −56.5 mV at 60 s and further to −54.5 mV at 120 s.

Next, the modified $3^{rd}$ SMEF (removing the activation overshoot electric pulse or the energy-trap overshoot electric pulse) was applied to the cell membrane through the voltage-clamp in clamping mode for 60 s (rectangular box). The fiber was held at the membrane resting potential right before switching to the clamp mode. Once the field application is over, the voltage-clamp was changed to the monitor model to measure the membrane potential change. The field-induced membrane potential change is shown as traces 310 and 315 superimposed with traces 300, and 305 in FIGS. 9A, and 9B, respectively. In the presence of normal ATP concentration, the field application depolarized the membrane potential for 1.5 mV (310). Once the field application was removed, membrane potential was depolarized merging to the membrane resting potential (300). In the presence of extremely low ATP, there was no membrane hyperpolarization, after removal of the electric field, again, the membrane potential (315) quickly merged to the control (305) without the field application.

Next, the synchronization oscillating electric field of the present invention, the $3^{rd}$ SMEF, with the magnitude of activation overshoot of 100 mV was applied to the cell membrane through a voltage-clamp for 60 s (rectangular box). The results are shown as traces 320 and 325 superimposed with the traces 300 and 305 as the control. In the presence of ATP molecules, the oscillating electric field hyperpolarized the membrane potential for about 1.5 mV (320). Once the electric field is over, the membrane potential gradually returned to the resting membrane potential. Interestingly, in the presence of extremely low ATP, the electrical field also hyperpolarized the membrane potential for about the same value (325). Then, the membrane potential was quickly depolarized until parallel to 305 but maintaining a 2.5 mV difference 330. Clearly, the $3^{rd}$ SMEF of the present invention protects the membrane potential depolarization, or the field-induced activation of the Na/K pumps can effectively maintain the membrane potential at extremely low concentrations of ATP.

In an experimental embodiment, the semitendinosus muscles from bullfrogs or the rat soleus muscles were first isolated, and then mounted on a force transducer in thermostat chambers containing KR buffer with 4 mm K+. The muscles were adjusted to optimal length for measurement of isometric contractions. To generate the muscle fatigue, a train of 0.2 or 1.0 ms pulses at supramaximal voltage (1.0-1.2 V) was applied to repeatedly stimulate the nerve that innervated the muscles at the frequency and duration indicated. For the field application, the muscles are non-invasively exposed to the $3^{rd}$ forward SMEF oscillating electric field via platinum wire electrodes placed on either side of the central region.

To evaluate contractile endurance, the initial muscle contract force decline recorded over the first 20 s of stimulation at 60 Hz was measured. From this measurement, the rate of force decline was calculated using the expression (Initial force decline (g s$^{-1}$)/Initial peak force (g))×100% and given as percent-per-second of peak force measured 1s after the onset of 60 Hz stimulation. This definition of the rate of force decline was used in all experiments. Obviously, if the rate of force decline is increasing, contractile endurance is reduced.

It was found that when exposed to physiological solution of $[K]_o$ (to 8-10 mm), the isolated rat soleus muscles show a pronounced reduction in contractile endurance. The inhibitory effect of elevated $[K]_o$ on sub tetanic contractions in isolated rat soleus is slow in onset, reflecting the diffusional delay for K+ ions to reach all fibers in the muscle, the lumen of the T-tubules, as well as the clearance of interstitial K ions via the Na/K pumps.

Similarly, under intense exercise until fatigue, interstitial K ions undergoes a progressive increase until it reaches concentrations of 10-12 mm where it can be assumed that excitability is lost and therefore the muscle cells cease to release K ions into the extracellular space.

This functional impairment is, to a large extent, counterbalanced by intracellular Na ions loading or the addition of compounds known to stimulate the Na/K pumps in the same muscle.

In the first group of experiments, the effects of the $3^{rd}$ forward SMEF on the membrane resting potential of semitendinosus muscle isolated from bullfrogs was studied. A micro-electrode first reads the potential in the path solution (adjusted to zero), and then is punctured into the muscle fiber to measure the membrane potential. After the electrode was withdrawn from the muscle, a series of stimulation pulses were applied to the nerves that innervate the muscle to generation muscle contractions until fatigue, marked by significant depolarization of the membrane potential. Then, the $3^{rd}$ forward SMEF was applied to the muscle fiber through a pair of linear electrodes in the solution parallel to the muscles. Once the electric field was removed, the muscle potential difference was remeasured.

Figure 4:
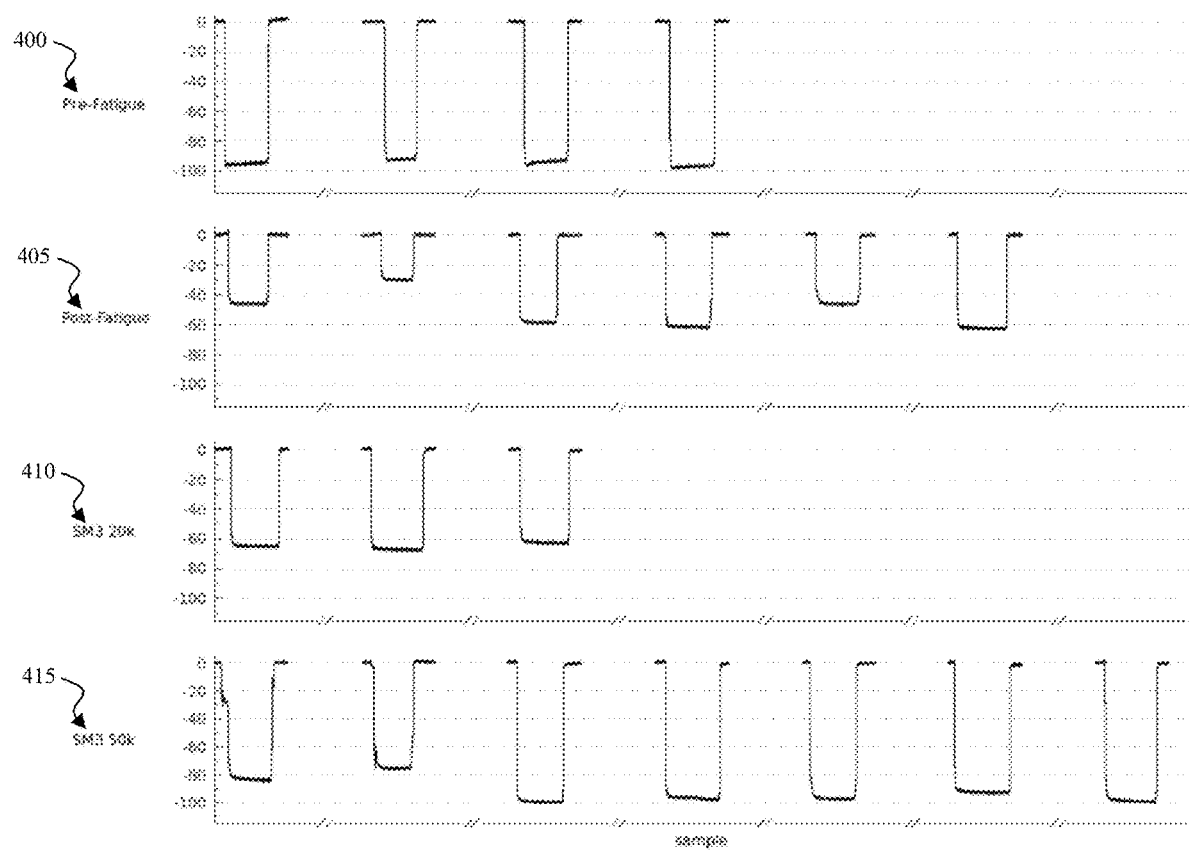
FIG. 4 illustrates the synchronization modulation electric field induced changes in the membrane potential of skeletal muscle fibers, in accordance with embodiments of the present invention.

FIG. 4 shows the results of the experiment described above. The pre-fatigue graphical illustration 400 of FIG. 4 shows the measured membrane potential from the muscles. The average potential difference was about −94 mV (n=4 fibers). After fatigue the membrane potential was depolarized to about −50 mV (n=6 fibers), as shown in the post-fatigue graphical illustration 405 of FIG. 4. With application of the $3^{rd}$ forward SMEF for nearly three minutes the membrane potential was recovered to about −60 mV, as shown in the SM3 20k graphical illustration 410 (2000 pulses, n=3 fibers) of FIG. 4, for eight minutes field application, the average potential difference was fully recovered to −92 mV as shown in the SM3 50k graphical illustration 415 SM3 (5000 pulses, n=7 fibers) of FIG. 4. The potential difference was retested 45 minutes later and the result had not changed in that time. This experiment was repeated for a total of seven times, and in all trials, it was shown that membrane potential can be significantly recovered.

In the second group of experiments, the contractile force of isolated semitendinosus bullfrog muscles was recorded. In these experiments the isolated muscle was tied at one end to the bottom of a vertical chamber filled with Normal Ringer's solution, and the other end was tied to a force sensor. Fatigue was induced by repeatedly stimulating the nerve that innervates these muscles and synchronization-modulation was applied to four electrodes that surround the whole muscle complex.

Figure 5:
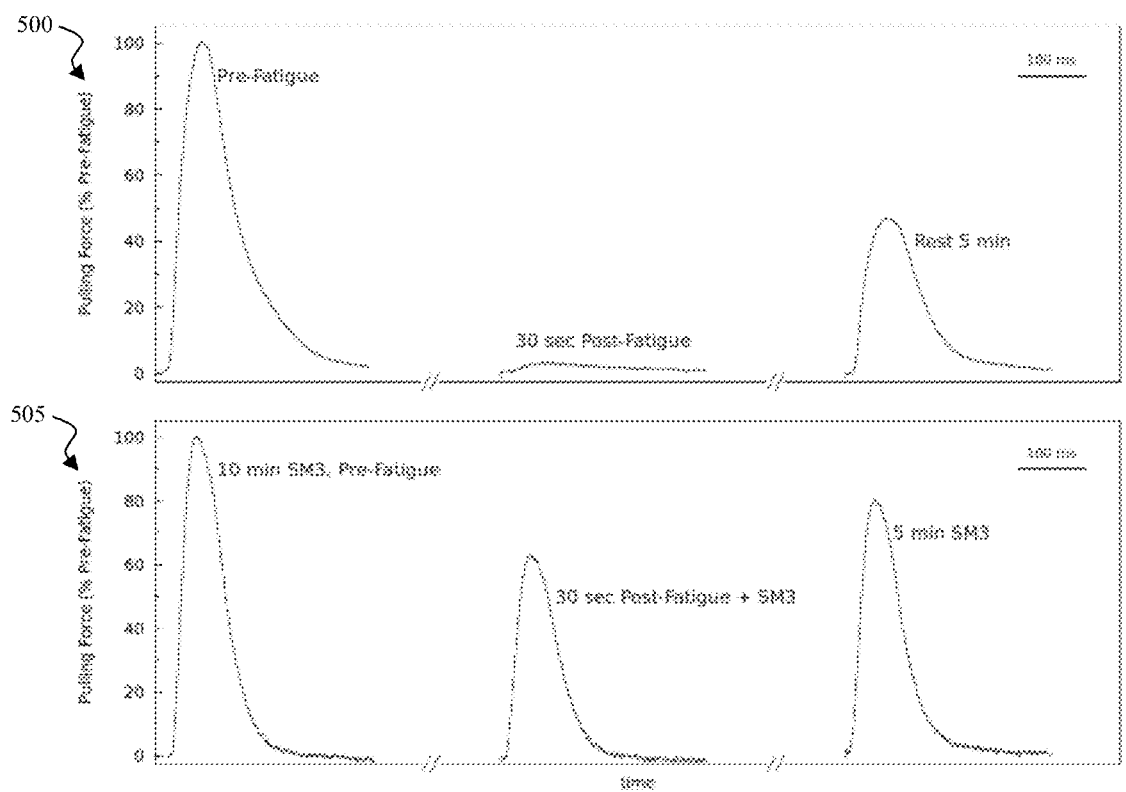
FIG. 5 illustrates muscle contractile force changes after overload exercises when the synchronization modulation technique of the present invention is applied, in accordance with embodiments of the present invention.

Graphical illustration 500 of FIG. 5 shows the control without the electric field application of the present invention. As shown, the muscle pulling force was recorded before, right after, and 5 minutes later for the muscle fatigue. Thirty seconds after the muscle fatigue, the contractile force is reduced to less than 10% of the pre-fatigue value. After five minutes relaxation, the pulling force was recovered to about 50% of the pre-fatigue contractile force. Graphical illustration 505 of FIG. 5 shows the application of the $3^{rd}$ forward SMEF of the present invention on the muscle pulling force. The field was applied throughout the whole procedure including muscle fatigue stimulation and the recovery time. As shown, with the electric field application, after the same fatigue stimulations pulling force remained at approximately 60% as strong as it was before fatigue, and five minutes later, the pulling force was recovered to 75% of the pre-fatigue contractile force.

As such, as shown in FIG. 5, in the first group 500, the contractile force is significantly diminished even 30 seconds after fatigue. After five minutes relaxation, the pulling force only recovered 50%. In the second group 505, the $3^{rd}$ forward SMEF was applied for ten minutes before, during, and after the applied fatigue stimulation. With the application of $3^{rd}$-SMEF, the muscle's contractile force did not diminish and was able to recover more.

Figure 6:
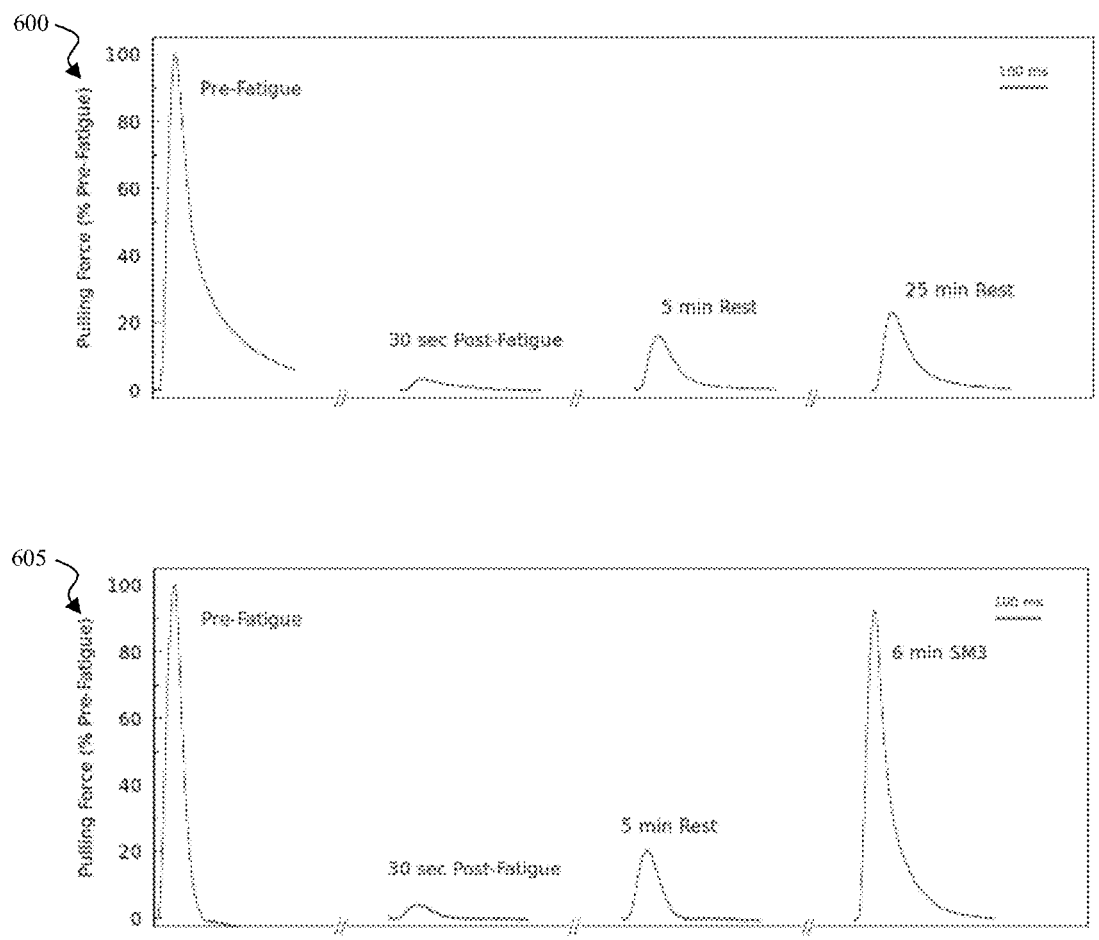
FIG. 6 illustrates the muscle recover from muscle fatigue with and without the application of the 3rd generation synchronization modulation technique, in accordance with embodiments of the present invention.

In this second group of experiments illustrated in FIG. 5, the $3^{rd}$ forward SM was applied to the muscles only after the muscle was fatigued in order to illustrate how the electric field accelerates the recovery from fatigue. Graphical illustration 600 of FIG. 6 shows the control without the electric field application. After 25 minutes recovery, the muscle pulling force only recovered to a little over 20% of the value before the muscle fatigue. However, the muscle contractile force was able to quickly recover by more than 90% after a six-minute application of the $3^{rd}$ forward SMEF, as shown in graphical illustration 605 of FIG. 6.

Large numbers of studies of human beings have concluded that intensive exercise and heavy work loading induced muscle fatigue are directly related to the function of the Na/K pumps, including the repeated high intensity activities, incremental exercise and in submaximal cycling ranging from 70 to 90% peak oxygen uptake. Clearly, maintenance and activation of Na/K pumps is critical to muscle fatigue.

In the following description, the $3^{rd}$ generation forward synchronization modulation electric field (SMEF) of the present invention was applied to the bicep muscle of volunteers in order to study its effects on muscle fatigue. In the first group of experiments, the functions of the muscles were measured by monitoring and analyzing the electromyograph (EMG). The median frequency of the power spectrum, the EMG travel time, which is inversely proportional to the membrane conduction velocity, and the Dimitrov fatigue index were calculated before and after the exercise for comparison with and without the $3^{rd}$ generation forward synchronization modulation electric field application. It was found that the SMEF electric field reduces about 20% of the shift in the median power frequency (MPF), the travel time, and the Dimitrov fatigue index. The results imply that the synchronization modulation electric field may be effective in reducing muscle fatigue.

In a particular experiment, ten participants were recruited to record the electromyograph (EMG) of their forearm performing a static contraction, both with and without the $3^{rd}$ SMEF. Fatigue was induced by asking the participants to squeeze an exercise handle for as long as possible and with a constant grip. Then, after several hours of rest, they would repeat the exercise for the same amount of time while the $3^{rd}$ forward SMEF of the present invention was applied. The EMG was recorded at the beginning and the end of each exercise, and then compared.

It was found that seven metrics of fatigue that can be computed from the EMG can then be used to gauge the amount of fatigue. The seven metrics of fatigue are: the root-mean-square, the median power frequency, the Dimitrov fatigue index, and four metrics of recurrence plot analysis (average diagonal and vertical line length, and the diagonal and vertical entropy). It was found that in nearly all the cases, application of the $3^{rd}$-SMEF resulted in less of a change in those metrics. As such, the electromyograph in an exercising forearm of a person shows signs of less fatigue with the application of the $3^{rd}$ forward SMEF technique of the present invention.

In the second group of specific experiments, the recovery of the compound muscle action potential (CMAP) was recorded. The ulnar nerve in the medial groove between the short head of the biceps and the long head of the triceps was supra-maximally stimulated to illicit contractions, and therefore fatigue, in the forearm muscle complex. The CMAP was also recorded in the forearm after stimulating this nerve.

Figure 7:
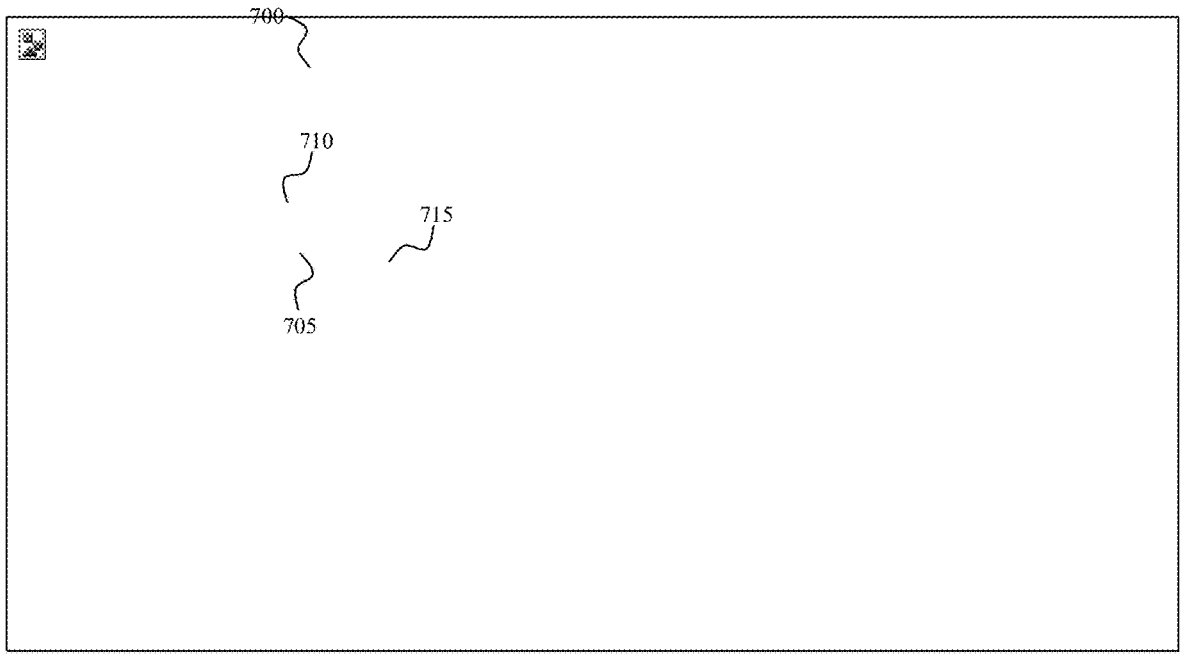
FIG. 7 illustrates examples of changes of the compound muscle action potential (CMAP) after overload exercises with the 3rd generation synchronization modulation technique applied, in accordance with embodiments of the present invention.

FIG. 7 illustrates examples of the CMAP before fatigue 700 (pre-fatigue), and then after six minutes of: rest 705 (rest 6 min), the random frequency changed for the $3^{rd}$-SMEF 720 (Rand3 6 min)), and the $3^{rd}$ forward SMEF 715 (SM3 6 min). As shown, tven though the $3^{rd}$ forward SMEF trial was performed last, its application is able to fully recover the CMAP after only six minutes, whereas the non-stimulated rest or a random frequency could not.

Figure 8:
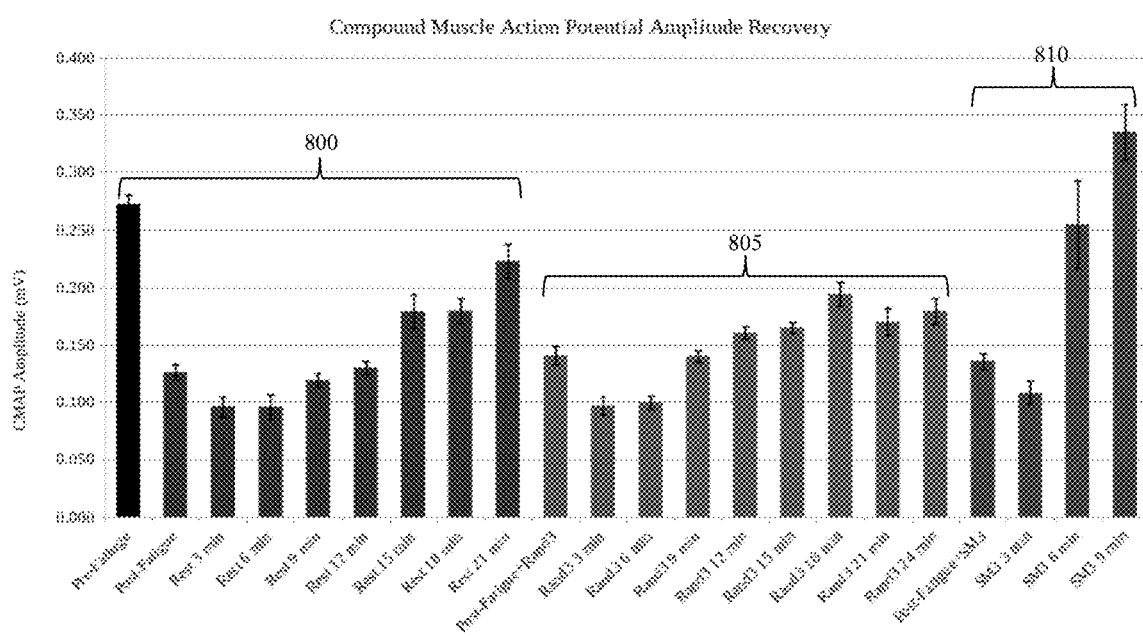
FIG. 8 is a chart illustrating the recovery of the CMAP's amplitude over time after overload exercises, in response to different electric stimulation, in accordance with embodiments of the present invention.

The chart in FIG. 8 shows the recovery of the CMAP's amplitude over time. In 800, the CMAP is allowed to recover without any stimulation. Then, in 805, the experiment is repeated, except that the CMAP recovers with the application of a random frequency. Then, in 810, the CMAP recovers with the $3^{rd}$ forward SMEF (SM3). As shown, for the control without field application 800, twenty minutes after fatigue, CMAP did not fully recover, similarly for the application of the randomly frequency-change electric field 805. In contrast, six minutes application of the $3^{rd}$ forward SMEF 810 almost fully recover CMAP, and nine minutes application makes the magnitude of CMAP larger than the control without fatigue.

The results show if the muscle is allowed to recover without any stimulation, it takes 20 minutes or more for the CMAP to fully recover, and the same is true if a random waveform is applied. However, if the $3^{rd}$ forward SMEF of the present invention is applied, the CMAP fully recovers after 6 to 9 minutes of application as shown in FIG. 7, FIG. 8 and FIG. 9.

Figure 9:
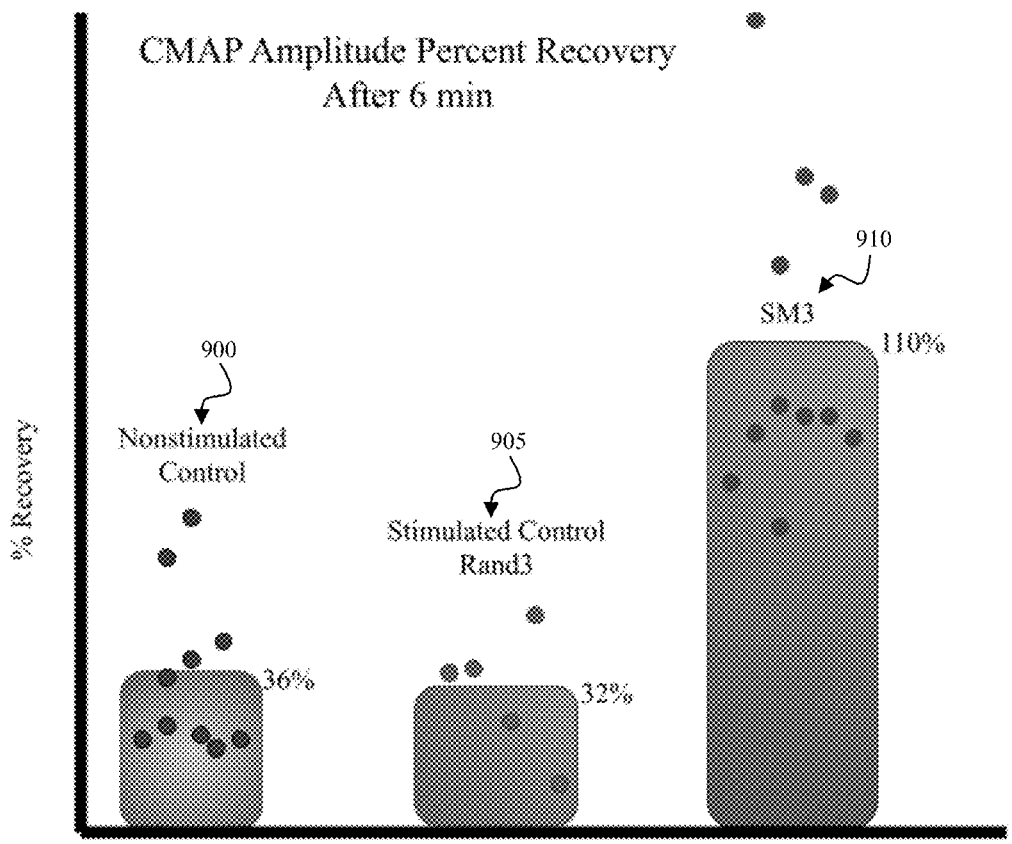
FIG. 9 is a chart illustrating the statistics of the percent recovery of the CMAP after overload exercises with and without application of the 3rd generation synchronization modulation electric field, in accordance with embodiments of the present invention.

The chart in FIG. 9 shows the statistics of the percent recovery of the CMAP after six minutes with rest only 900, application of random frequency 905, or the $3^{rd}$ forward SMEF 910. On average, after six minutes application of $3^{rd}$ forward SMEF the CMAP has more than fully recovered, whereas the CMAP recovers by about a third with rest or random frequency.

Figure 10:
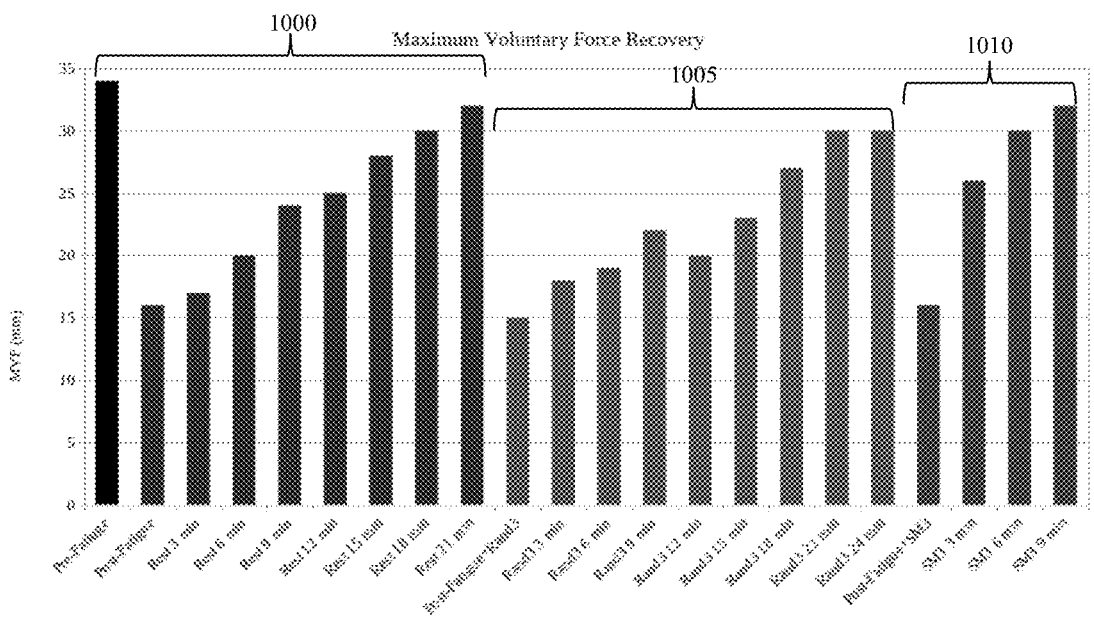
FIG. 10 is a chart illustrating the recovery of the maximum voluntary force (MVF) after muscle fatigue induced by the overload exercises, in accordance with embodiments of the present invention.

In addition, after each CMAP measurement, the participant was asked to squeeze an exercise handle as strongly as they could using only two of their fingers, and the distance that they could squeeze the handle was used as a metric of force generating capability, which is called the maximum voluntary force (MVF). FIG. 10 shows that recovery of the MVF with rest only 1000, application of random frequency 1005 and the $3^{rd}$ SMEF 1010. As shown, the recovery of the MVF closely follows the recovery of the CMAP, and this group of experiments showed that the compound muscle action potential can recover only after six minutes of application of the $3^{rd}$ forward SMEF 1010 of the present invention.

The chart in FIG. 10 shows the recovery of the MVF in a manner similar to the recovery of the CMAP in FIG. 8. It is necessary to point out the different scale in X-axis. For both control without the field application and the application of random frequency change field, MVF takes over 20 minutes to fully recover, while under the $3^{rd}$ forward SMEF it only takes 9 minutes.

In the third group of experiments, static contractarians were performed in the forearm and bicep of participants, and the time to fatigue was recorded. Participants were recruited to either squeeze an exercise handle or hold a dumbbell at a 90° angle for as long as possible. The experiments were performed in blind for the participants. The participants were able to hold the static contraction 56% and 49% longer when the $3^{rd}$ forward SMEF was applied when compared to a control trial. However, when a random frequency or alternative synchronization-modulation technique was applied, instead of the $3^{rd}$ forward SMEF of the present invention, there was no improvement over the non-stimulated control trial. As such, this group of experiments showed that the time-to-fatigue increases in static forearm and bicep contractions.

Figure 11:
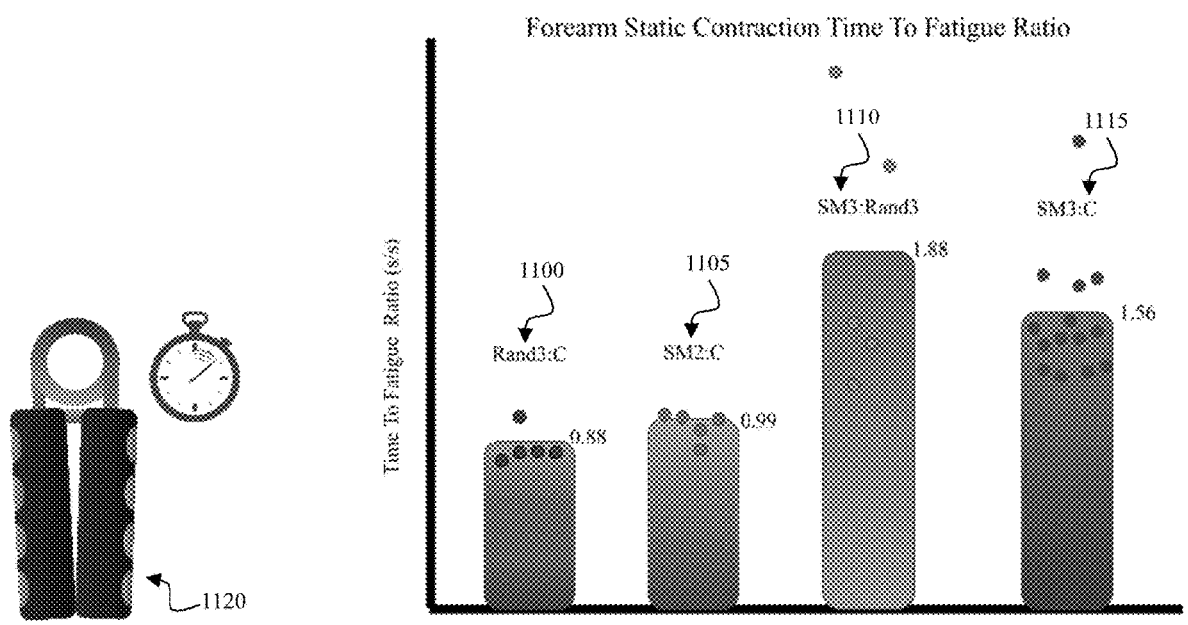
FIG. 11 is an illustration of the time to fatigue ratio in the forearm with various types of stimulation, in accordance with embodiments of the present invention.

FIG. 11 illustrates the time to fatigue ratio in the forearm with various types of stimulation. Rand3:C=stimulation with random frequency vs. non-stimulated control 1100. SM2:C=an alternative second-generation synchronization-modulation (removal of the activation overshoot electric pulse) vs. non-stimulated control 1105. SM3:Rand3 stimulation with the third-generation forward synchronization-modulation electric field of the present invention vs. random frequency 1110. SM3:C stimulated with third-generation forward synchronization-modulation electric field of the present invention vs. non-stimulated control. On average, participants can squeeze the exercise handle 1120 56% longer with application of the $3^{rd}$ forward SMEF of the present invention when compared to no stimulation.

Figure 12:
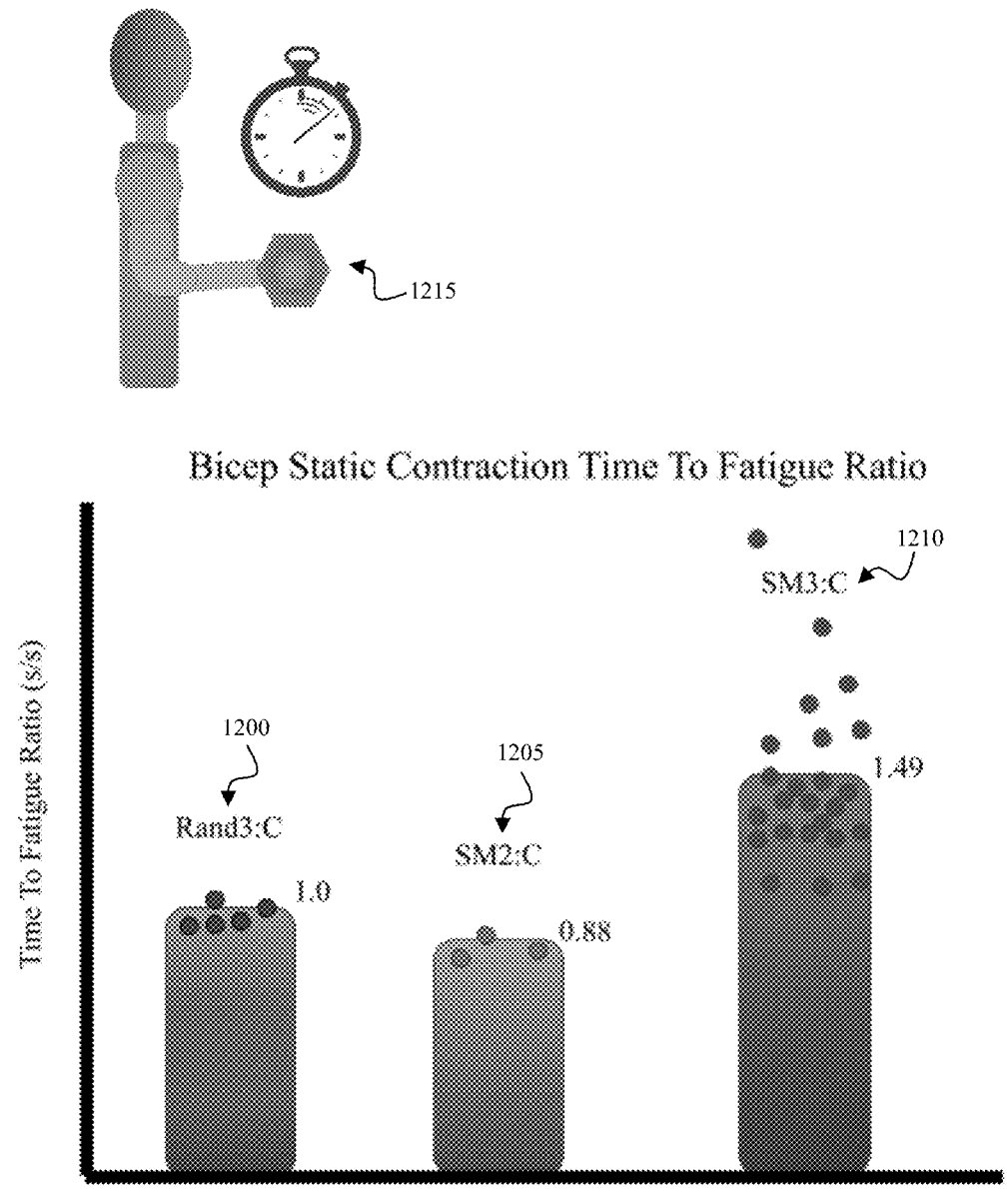
FIG. 12 is an illustration of the time to muscle fatigue in the bicep with various types of stimulation, in accordance with embodiments of the present invention.

FIG. 12 illustrates the time to fatigue ratio in the bicep with various types of stimulation. Rand3:C=stimulation with random frequency vs. non-stimulated control 1200. SM2:C=an alternative second-generation synchronization-modulation vs. non-stimulated control 1205. SM3:C=the third-generation forward synchronization modulation technique of the present invention vs non-stimulated control 1210. On average, participants can perform bicep curls 1215 49% longer with application of the $3^{rd}$ forward SMEF technique of the present invention, when compared to no stimulation.

Figure 13:
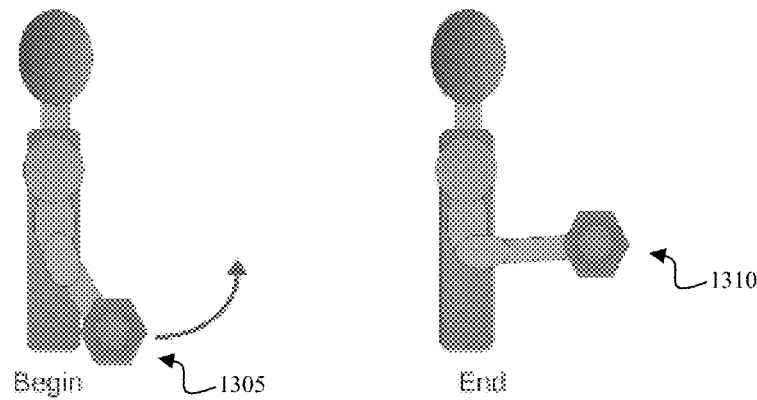
FIG. 13 is an illustration of the performance for bicep curls responding to the overload exercises with and without application of the synchronization modulation technique, in accordance with embodiments of the present invention.
Figure 13:
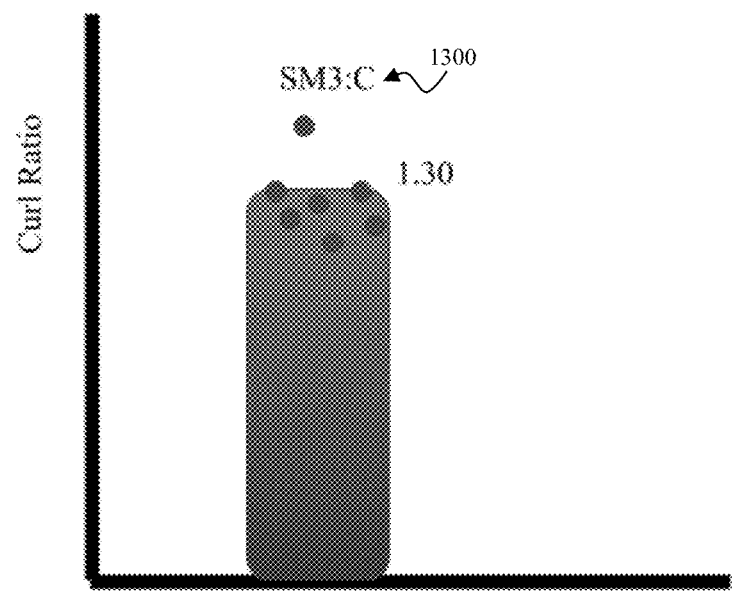

As shown in FIG. 13, participants were recruited to perform bicep curls comprising a begin position 1305 and an ending position 1310, and in seven trials we found that they could do 16%-55% more curls with the application of the $3^{rd}$ forward SMEF (SM3) technique of the present invention 1300 (mean=30).

In summary, the synchronization modulation of the Na/k pumps in accordance with the embodiments of the present invention is an innovative, rigorous technique to protect or alleviate muscle fatigue.

As such, in various embodiments, the present invention provides a system and method for controlling the Na/K pumps by applying an energy generating synchronization modulation electric field, referred to as the $3^{rd}$ forward SMEF, which not only synchronizes the active ion transporter, but also synthesizes ATP to provide enough energy to the pump molecules. The synchronization modulation electric field of the present invention has been shown to be effective in addressing muscle fatigue.

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C#, C++, Visual Basic or the like and conventional procedural programming languages, such as the "C" programming language or similar programming languages.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims.

What is claimed is:

1. A method for controlling active ion transporters for the treatment or prevention of muscle fatigue, the method comprising:
   applying an oscillating electric field to one or more active ion transporters of one or more muscle tissues, wherein the oscillating electric field comprises three serially applied phases and wherein applying the oscillating electric field comprises;
   applying a synchronization phase to synchronize the active ion transporters to a physiological turnover rate of the active ion transporters down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter is in a negative half-cycle and the ion-extrusion half-cycle of the active ion transporter is in a positive half-cycle of the oscillating electric field and wherein applying the synchronization phase further comprises:

applying an activation overshoot electric pulse at a start of the negative half-cycle and at a start of the positive half-cycle of the oscillating electric field;

applying an energy-trap overshoot electric pulse at an end of the negative half-cycle and at an end of the positive half-cycle of the oscillating electric field; and applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;

applying a modulation phase to modulate the synchronized active ion transporters to a predetermined target turnover rate; and applying a maintenance phase to maintain the synchronized active ion transporters at the predetermined target turnover rate for a predetermined duration of time.

2. The method of claim 1, wherein one ATP molecule is consumed during the running cycle of the one or more active ion transporters and one ATP molecule is synthesized during the running cycle of the active ion transporters, resulting in the net-consumption of ATP of the active ion transporters being substantially equal to zero during the running cycle.

3. The method of claim 1, wherein the one or more active ion transporters is a Na/K pump.

4. The method of claim 1, wherein the one or more muscle tissues are selected from smooth muscle tissue and skeletal muscle tissue.

5. The method of claim 1, wherein the synchronization phase further restricts an outward transporter current at the start of the activation overshoot electric pulse in the positive half-cycle and restricts an inward transporter current at the start of the activation overshoot electric pulse in the negative half-cycle of the oscillating electric field.

6. The method of claim 1, wherein a membrane potential of the active ion transporters is hyperpolarized in response to the activation overshoot electric pulse and the energy-trap overshoot electric pulse during the negative half-cycle of the oscillating electric field, and wherein the membrane potential of the active ion transporters is depolarized in response to the activation overshoot electric pulse and the energy-trap overshoot electric pulse during the positive half-cycle of the oscillating electric field.

7. The method of claim 1, wherein a magnitude of the activation overshoot electric pulse is sufficient to allow the active ion transporters to operate within a physiological range of a membrane potentials of the active ion transporters and wherein a magnitude of the energy-trap overshoot electric pulse is sufficient to allow the active ion transporters to operate within a physiological range of the membrane potentials of the active ion transporters.

8. The method of claim 1, wherein a duration of the activation overshoot electric pulse is about 1 ms or less, a magnitude of the activation overshoot electric pulse is at least about 90 mV, a duration of the energy-trap overshoot electric pulse is about 1.5 ms or less, a magnitude of the energy-trap overshoot electric pulse is about 70 mV and the electric field plateau is about 20 mV between the activation overshoot electric pulse and the energy-trap overshoot electric pulse.

9. The method of claim 1, wherein a frequency of the oscillating electric field during the synchronization phase is substantially equal to the physiological turnover rate of the active ion transporters.

10. The method of claim 1, wherein applying the modulation phase further comprises:

applying an oscillating electric field wherein waveform of the oscillating electric field is identical as the oscillating electric field in the synchronization phase, and the magnitude of the activation overshoot electric pulse and the energy-trap overshoot electric pulse is the same as the magnitude of the activation overshoot electric pulse and the energy-trap overshoot electric pulse in the synchronization phase, respectively, and the duration of the activation overshoot electric pulse and the energy-trap overshoot electric pulse is the same as the duration of the activation overshoot electric pulse and the energy-trap overshoot electric pulse in the synchronization phase, respectively.

11. The method of claim 1, wherein applying the modulation phase further comprises applying a forward modulation wherein a frequency of the oscillating electric field is gradually increased to accelerate a turnover rate of the active ion transporters to the predetermined target turnover rate and applying a backward modulation wherein the frequency of the oscillating electric field is gradually decreased to decelerate the active ion transporters to the predetermined target turnover rate.

12. The method of claim 11, wherein gradually increasing and decreasing the frequency of the oscillating electric field is performed in a stepwise pattern, where the frequency is changed from about 3% to about 10% and repeated for approximately 5 to 10 oscillating pulses at the frequency.

13. The method of claim 1, wherein applying the maintenance phase comprises applying a waveform and a frequency of the oscillating electric field that is equivalent to a waveform and a frequency of the oscillating electric field applied during the modulation phase.

14. A system for controlling active ion transporters for the treatment or prevention of muscle fatigue, the system comprising:

an electric field generator to generate and apply an oscillating electric field to one or more active ion transporters of one or more muscle tissues, wherein the oscillating electric field comprises three serially applied phases and applying the oscillating electric field comprises;

applying a synchronization phase to synchronize the active ion transporters to a physiological turnover rate of the active ion transporter down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter is in a negative half-cycle and the ion-extrusion half-cycle of the active ion transporter is in a positive half-cycle of the oscillating electric field and wherein applying the synchronization phase further comprises:

applying an activation overshoot electric pulse at a start of the negative half-cycle and at a start of the positive half-cycle of the oscillating electric field;

applying an energy-trap overshoot electric pulse at an end of the negative half-cycle and at an end of the positive half-cycle of the oscillating electric field; and applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;

applying a modulation phase to modulate the synchronized active ion transporters to a predetermined target turnover rate; and applying a maintenance phase to maintain the synchronized active ion transporters at the predetermined target turnover rate for a predetermined duration of time.

15. The system of claim 14, wherein one ATP molecule is consumed during the running cycle of the active ion transporters and one ATP molecule is synthesized during the running cycle of the active ion transporters, resulting in the net-consumption of ATP of the active ion transporters being substantially equal to zero during the running cycle.

16. The method of claim 14, wherein the one or more active ion transporters is a Na/K pump.

17. A non-transitory computer-readable medium storing a set of instructions configured for being executed by at least one processor for performing a method for controlling one or more active ion transporters of one or more muscle tissues, the method comprising: controlling an electric field generator to apply an oscillating electric field to the one or more active ion transporters, wherein the oscillating electric field comprises three serially applied phases and wherein applying the oscillating electric field comprises;

applying a synchronization phase to synchronize the active ion transporters to a physiological turnover rate of the active ion transporters down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter is in a negative half-cycle and the ion-extrusion half-cycle of the active ion transporter is in a positive half-cycle of the oscillating electric field and wherein applying the synchronization phase further comprises:

applying an activation overshoot electric pulse at a start of the negative half-cycle and at a start of the positive half-cycle of the oscillating electric field;

applying an energy-trap overshoot electric pulse at an end of the negative half-cycle and at an end of the positive half-cycle of the oscillating electric field; and applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;

applying a modulation phase to modulate the synchronized active ion transporters to a predetermined target turnover rate; and applying a maintenance phase to maintain the synchronized active ion transporters at the predetermined target turnover rate for a predetermined duration of time.

18. The non-transitory media of claim 17, wherein one ATP molecule is consumed during the running cycle of the active ion transporters and one ATP molecule is synthesized during the running cycle of the active ion transporters, resulting in the net-consumption of ATP of the active ion transporters being substantially equal to zero during the running cycle.

* * * * *